US00PP36123P3

(12) United States Plant Patent
Schoone

(10) Patent No.: US PP36,123 P3
(45) Date of Patent: Sep. 17, 2024

(54) ***PHALAENOPSIS* PLANT NAMED 'BABBLE BEACH'**

(50) Latin Name: *Phalaenopsis hybrida*
Varietal Denomination: Babble Beach

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/527,336

(22) Filed: Dec. 3, 2023

(65) Prior Publication Data

US 2024/0188465 P1 Jun. 6, 2024

Related U.S. Application Data

(60) Provisional application No. 63/430,035, filed on Dec. 4, 2022.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
See application file for complete search history.

*Primary Examiner* — Susan McCormick Ewoldt
(74) *Attorney, Agent, or Firm* — C. Anne Whealy

(57) ABSTRACT

A new and distinct cultivar of *Phalaenopsis* plant named 'Babble Beach', characterized by its relatively compact and upright plant habit; moderately vigorous growth habit; strong flowering stems; strong leaves; freely flowering habit with typically five inflorescences developing per plant, each inflorescence with numerous flowers; flowers with white-colored petals and white-colored sepals that are slightly blushed with yellow; flowers with white and yellow-colored labella; and good postproduction longevity.

2 Drawing Sheets

Figure 1:
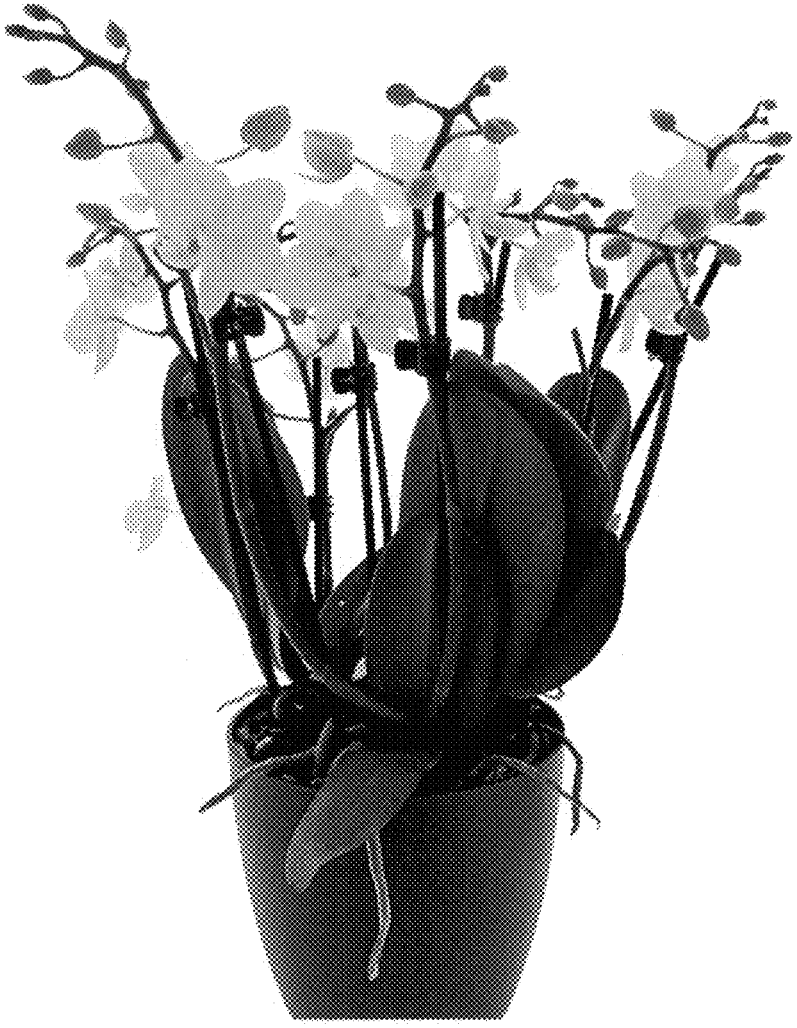

Botanical designation: *Phalaenopsis hybrida.*
Cultivar denomination: 'BABBLE BEACH'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B. V. of Heemskerk, The Netherlands on Aug. 15, 2022, application number 2022/1909. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Babble Beach'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in May, 2012, in Assendelft, The Netherlands of a proprietary selection of *Phalaenopsis hybrida* identified as code number 4521, not patented, as the female, or seed, parent with a proprietary selection of *Phalaenopsis hybrida* identified as code number 4325-1, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in January, 2018.

Asexual reproduction of the new *Phalaenopsis* plant by in vitro meristem propagation in a controlled environment in Assendelft, The Netherlands since January, 2019 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Babble Beach'. These characteristics in combination distinguish 'Babble Beach' as a new and distinct *Phalaenopsis* plant:

1. Relatively compact and upright plant habit.
2. Moderately vigorous growth habit.
3. Strong flowering stems.
4. Strong leaves.
5. Freely flowering habit with typically five inflorescences developing per plant, each inflorescence with numerous flowers.
6. Flowers with white-colored petals and white-colored sepals that are slightly blushed with yellow.
7. Flowers with white and yellow-colored labella.
8. Good postproduction longevity.

Plants of the new *Phalaenopsis* can be compared to plants of the female parent selection. Plants of the new *Phalaenopsis* differ primarily from plants of the female parent selection in the following characteristics:

1. Flower petals of plants of the new *Phalaenopsis* are imbricate whereas flower petals of plants of the female parent selection are not imbricate.
2. Flower sepals of the plants of the new *Phalaenopsis* are slightly blushed with yellow whereas flower sepals of plants of the female parent selection are pure white in color.

Plants of the new *Phalaenopsis* can be compared to plants of the male parent selection. Plants of the new *Phalaenopsis* differ primarily from plants of the male parent selection in the following characteristics:

1. Flower petals of plants of the new *Phalaenopsis* are imbricate whereas flower petals of plants of the male parent selection are not imbricate.
2. Flower sepals of the plants of the new *Phalaenopsis* are slightly blushed with yellow whereas flower sepals of plants of the male parent selection are pure white in color.

Plants of the new *Phalaenopsis* can be compared to plants of *Phalaenopsis hybrida* 'Snow Cloud', not patented. In side-by-side comparisons, plants of the new *Phalaenopsis* differ primarily from plants of 'Snow Cloud' in the following characteristics:

1. Flower petals of plants of the new *Phalaenopsis* are imbricate whereas flower petals of plants of 'Snow Cloud' are not imbricate.
2. Flower sepals of the plants of the new *Phalaenopsis* are slightly blushed with yellow without any spots whereas flower sepals of plants of 'Snow Cloud' are pure white in color with a few spots.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Babble Beach' grown in a container.

Figure 2:
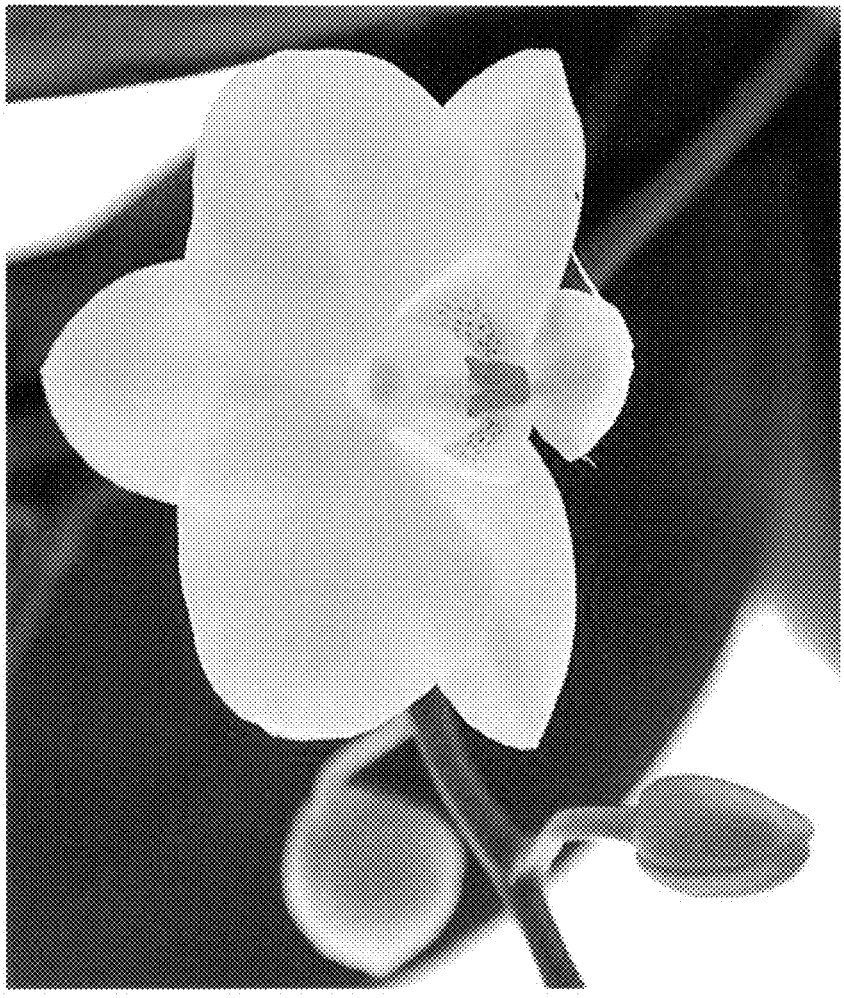

The photograph on the second sheet (FIG. 2) is a close-up view of typical flower buds and a typical flower of 'Babble Beach'.

DETAILED BOTANICAL DESCRIPTION

The aforementioned photographs and following observations and measurements describe plants grown during the summer with two plants in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27C. During the final six months of production of the plants, day temperatures ranged from 20C to 22C and night temperatures ranged from 18C to 20C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Babble Beach'.

Parentage:

*Female, or seed, parent.*—Proprietary selection of *Phalaenopsis hybrida* identified as code number 4521, not patented.

*Male, or pollen, parent.*—Proprietary selection of *Phalaenopsis hybrida* identified as code number 4325-1, not patented.

Propagation:

*Type.*—By in vitro meristem propagation.

*Time to initiate roots, summer and winter.*—About two weeks at temperatures about 28C to 30C.

*Time to produce a rooted young plant, summer and winter.*—About 20 to 25 weeks at temperatures about 28C to 30C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically five inflorescences developing per plant, each inflorescence with numerous flowers; monopodial; moderately vigorous growth habit and moderate growth rate.

*Plant height, substrate level to top of foliar plane.*—About 13.5 cm.

*Plant height, substrate level to top of floral plane.*—About 24 cm.

*Plant diameter or spread.*—About 21.7 cm.

Leaf description:

*Arrangement and quantity.*—Distichous, simple; sessile; about four leaves per plant.

*Length.*—About 14.2 cm.

*Width.*—About 7 cm.

*Aspect.*—Outwardly arching.

*Shape.*—Obovate; slightly carinate.

*Apex.*—Unequal acute to unequal emarginate.

*Base.*—Sheathing. Sheath length: About 1 cm. Sheath width: About 1 cm. Sheath color: Close to 143C; marginal edges, close to 143B.

*Margin.*—Entire; not undulate.

*Texture and luster, upper and lower surfaces.*—Smooth, glabrous; moderately glossy.

*Venation pattern.*—Camptodromous.

*Color.*—Developing and fully expanded leaves, upper surface: Slightly darker than a blend of 143A and 146A; venation, darker than a blend of 143A and 146A. Developing and fully expanded leaves, lower surface: Close to 146B; venation, close to 143A and 143B.

Inflorescence description:

*Appearance and flowering habit.*—Showy zygomorphic flowers arranged on axillary simple or branched racemes; typically five inflorescences develop per plant; each inflorescence with about twelve flowers; flowers face outwardly on outwardly arching inflorescences supported by upright peduncles; flowers with three petals, two lateral petals and one center petal transformed into a labellum and three sepals.

*Fragrance.*—None detected.

*Time to flower.*—Plants begin flowering about six months after planting; plants flower naturally during the winter into the spring.

*Flower longevity.*—Long flowering period, individual flowers maintain good substance for about eight weeks on the plant; flowers not persistent.

*Inflorescence length* (*lowermost flower to inflorescence apex*).—About 10.5 cm.

*Inflorescence width.*—About 8.1 cm.

*Flower buds.*—Height: About 1.5 cm. Diameter: About 9 mm by 11 mm. Shape: Broadly ovate. Color: Close to 150C.

*Flower size.*—About 3.7 cm (vertical) by 4.2 cm (horizontal).

*Flower depth.*—About 1.9 cm.

*Petals, quantity and arrangement.*—Three, two lateral petals and one center petal transformed into a labellum.

*Lateral petals.*—Length: About 2.1 cm. Width: About 2.1 cm. Shape: Broadly ovate to close to reniform. Apex: Obtuse. Margin: Entire; not undulate. Texture and luster, upper and lower surfaces: Smooth, glabrous, velvety; matte. Color: When opening, upper surface: Close to N155B. When opening, lower surface: Close to N155B; centers, close to NN155A. Fully opened, upper and lower surfaces: Close to NN155D; color does not change with subsequent development.

*Labella.*—Appearance: Three-parted with two lateral lobes and a central lobe. Length, lateral lobes: About 1.2 cm. Width, lateral lobes: About 8 mm. Length, central lobe: About 1.5 cm. Width, central lobe: About 3 mm to 10 mm. Length, cirrhose tips: About 5 mm. Shape, lateral lobes: Obovate. Shape, central lobe: Ovate. Apex, lateral lobes: Obtuse. Apex, central lobe: Cleft with two laterally curved and slightly reflexed cirrhose apices. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 3 mm in length, about 4 mm in width and about 3 mm in height. Color: When opening, upper surface: Lateral lobes: Close to NN155B; at the base, tinged with close to 4D with sparse fine dots, close to N167C. Central lobe: Close to 4A and 4B; towards the apex, close to NN155D; cirrhose tips, close to NN155D; at the base, close to NN155C with sparse fine dots, close to 181B. Callosities: Close to 12A; sparse fine dots, close to 181B. When opening, lower surface: Lateral lobes: Close to NN155B; towards the proximal margins and base, close to NN155A. Central lobe: Close to 3B and 3C; towards the apex, close to NN155D; cirrhose tips, close to NN155D; at the base, close to 155A. Fully opened, upper surface: Lateral lobes: Close to NN155B; at the base, tinged with close to 4D with sparse fine dots, close to N167C. Central lobe: Close to 8B to 8D; towards the apex, close to NN155D; cirrhose tips, close to NN155D; at the base, close to NN155C with sparse fine dots, close to 181B. Callosities: Close to 13A; sparse fine dots, close to 181B. Fully opened, lower surface: Lateral lobes: Close to NN155D; towards the proximal margins and base, close to NN155C. Central lobe: Close to 3B and 3C; towards the apex, close to NN155D; cirrhose tips, close to NN155D; at the base, close to 155A.

*Sepals.*—Quantity and arrangement: Three, one upper dorsal sepal and two lower lateral sepals. Length, dorsal sepal: About 2.3 cm. Width, dorsal sepal: About 1.6 cm. Length, lateral sepals: About 2.3 cm. Width, lateral sepals: About 1.5 cm. Shape, dorsal sepal: Ovate to elliptic. Shape, lateral sepals: Ovate. Apex, dorsal sepal: Abruptly acute. Apex, lateral sepals: Acute. Base, dorsal and lateral sepals: Truncate. Margins, dorsal and lateral sepals: Entire; not undulate. Texture and luster, dorsal and lateral sepals, upper and lower surfaces: Smooth, glabrous, moderately velvety; matte. Color, dorsal sepal: When opening, upper surface: Close to NN155A. When opening, lower surface: Close to 155A; at the base, close to a blend of 155A and 150D. Fully opened, upper surface: Close to NN155D; proximally, blushed with close to 6A; color does not change with subsequent development. Fully opened, lower surface: Close to NN155C; color does not change with subsequent development. Color, lateral sepals: When opening, upper surface: Close to NN155B; proximally, close to 150D. When opening, lower surface: Close to 150D; proximally, close to 1C. Fully opened, upper surface: Close to a blend of 155C and NN155D; color does not change with subsequent development. Fully opened, lower surface: Close to NN155A; proximally, close to 155A; color does not change with subsequent development.

*Peduncles.*—Length: About 24.8 cm. Diameter: About 5 mm. Strength: Strong. Aspect: Upright to outwardly arching. Texture and luster: Smooth, glabrous; matte. Color: Close to a blend of 137C and 143B; fine dots, close to 138B.

*Pedicels.*—Length: About 2.6 cm. Diameter: About 2 mm. Strength: Moderately strong. Aspect: About 85 degrees from peduncle axis. Texture and luster: Smooth, glabrous; matte. Color: Close to 157D; distally, tinged with close to 151D and proximally, close to 144A and 144B; upper surface, slightly tinged with close to 65D.

*Reproductive organs.*—Androecium: Column length: About 6 mm. Column width: About 4 mm. Column color: Close to NN155B. Pollinia quantity: Two. Pollinia diameter (per two pollinia): About 2.5 mm. Pollinia color: Close to 23A. Gynoecium: Stigma length: About 3.5 mm. Stigma width: About 3 mm. Stigma shape: Reniform. Stigma color: Close to N155A. Ovary length: About 7 mm. Ovary diameter: About 0.75 mm. Ovary color: Close to 149C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40C and are suitable for USDA Hardiness Zones 10 to 12.

It is claimed:

1. A new and distinct *Phalaenopsis* plant named 'Babble Beach' as illustrated and described herein.

* * * * *